(12) United States Patent
Innes

(10) Patent No.: US 6,759,370 B1
(45) Date of Patent: Jul. 6, 2004

(54) HERBICIDES

(75) Inventor: Rodney Mitchell Innes, Te Kouma (NZ)

(73) Assignee: Organic Interceptor Products Limited, Ponsonby (NZ)

(*) Notice: Subject to any disclaimer, the term of this patent is extended or adjusted under 35 U.S.C. 154(b) by 0 days.

(21) Appl. No.: 09/673,987

(22) PCT Filed: Apr. 21, 1999

(86) PCT No.: PCT/NZ99/00047

§ 371 (c)(1),
(2), (4) Date: Jan. 8, 2001

(87) PCT Pub. No.: WO99/53764

PCT Pub. Date: Oct. 28, 1999

(30) Foreign Application Priority Data

Apr. 21, 1998 (NZ) .................................. 330283

(51) Int. Cl.⁷ .................. A01N 31/02; A01N 37/02; A01N 25/30
(52) U.S. Cl. .................. 504/142; 514/558; 514/729
(58) Field of Search .................. 504/142; 514/558, 514/729

(56) References Cited

U.S. PATENT DOCUMENTS

| | | | |
|---|---|---|---|
| 5,407,899 A | | 4/1995 | Howell .................. 504/152 |
| 5,728,672 A | * | 3/1998 | Richter .................. 510/463 |
| 5,753,593 A | * | 5/1998 | Pullen et al. .................. 504/150 |
| 5,763,468 A | * | 6/1998 | Barranx et al. .................. 510/383 |
| 5,948,731 A | * | 9/1999 | Evans et al. .................. 504/320 |

FOREIGN PATENT DOCUMENTS

| | | |
|---|---|---|
| AU | A-74210/96 | 9/1996 |
| BE | 1002598 A6 | 4/1991 |
| CA | 1153267 | 9/1983 |
| EP | 0 617 888 A1 | 2/1994 |
| GB | 1464716 | 3/1973 |
| WO | WO 91/05472 | 5/1991 |
| WO | WO 96/16549 | 6/1996 |
| WO | WO 97/16975 | 5/1997 |
| WO | WO 98/31223 | 7/1998 |

* cited by examiner

Primary Examiner—S. Mark Clardy
(74) Attorney, Agent, or Firm—Knobbe, Martens, Olson & Bear, LLP

(57) ABSTRACT

The presently claimed invention is directed to agricultural compositions which find primary use as a herbicide, through may also be used for pesticidal and fungicidal roles. The presently claimed invention comprises compositions combining monterpene compounds with fatty acid soaps. In particular monterpene alcohols are preferred as a primary phytoactive agent. Preferred embodiments are based on coniferous oils, such as pine oil, in combination with a tall oil reacted with an alkali to form a fatty acid soap. Preferred methods of application include spraying in a manner in which some foaming effect is observed, which appears to confer advantage over the spray application of monoterpene compounds alone.

36 Claims, No Drawings

HERBICIDES

This is the U.S. national phase under 35 U.S.C. §371 of International Application PCT/NZ99/00047, filed Apr. 21, 1999.

TECHNICAL FIELD

The present invention is directed to compositions exhibiting herbicidal activity. Many compositions also exhibit insecticidal and/or fungicidal activity and thus this is also a consideration of the present invention. Preferred embodiments of the present invention combine monoterpene alcohols with fatty acid soaps.

BACKGROUND ART

Farming is one manifestation of civilisation and thus for some time man has attempted to clear areas of land for horticulture and agriculture as well as control what type of plants establish themselves there. In earlier times the methods used focused on physical effort or fire to remove and control weeds or unwanted growth. As time progressed it was recognised that various types of chemicals had an adverse effect on many plants and were an efficient alterative to labour intensive methods of control. With the rapid advance of the chemical and petro-chemical industries in the $19^{th}$ and $20^{th}$ centuries, chemical sprays for the control of not only plants but also fungus and insects etc. proliferated. Currently there is a wide range of insecticides and herbicides available which are based solely or predominantly on synthetic chemicals.

However, of more recent times there has been increased consumer backlash against the use of synthetic products, or products which are perceived not to be of natural origin. This consumer resistance is at least partially based on problems and difficulties associated with the use of chemicals in agriculture. The use of insecticides is one graphic example where for some time the problems of residue run-off entering the eco-system has caused problems down the food chain. As a consequence, much research has gone into the development of new synthetic insecticides which address this problem—typically by the use of products which bio-degrade quickly in the environment and/or are less likely to interfere or harm animals further up the food chain. Another solution has been to place more dependence upon the use of naturally occurring insecticides, many of which have been found to occur naturally in plants.

Herbicides represent a different area and have different problems. Here there are still problems with run-off and residues. Toxicity to animals and humans is also a major problem. For instance, the use of herbicides of the paraquat family have been tightly controlled or banned in many countries.

Residues represent a problem insofar as it is often desirable to sow over cleared ground as soon as possible after defoliation. Many herbicides have a residual period before re-sowing or over-sowing can occur. A further problem relates to residual compounds in the dead foliage. These may remain in the foliage until bio-degraded or otherwise eliminated into the environment. Having to physically remove dead foliage to allow immediate resowing is not a viable option in most instances.

The art has sought to address many of these problems. The glyphosate family of herbicide are very important commercially and are widely used where compounds of low toxicity and short residual life time in the soil are required. However, these compounds still represent synthetic products which are still resisted by the public's swing to naturally based products and organic farming.

While many insecticidal compounds occur naturally and have been identified (e.g. the pyrethrins) there is no such plant based herbicidal compounds in the art. This perhaps appears not to be surprising, for while many plants have evolved to produce compounds which repel or kill insects which may affect them, it is relatively uncommon, if at all observed, for plants to have to control other plants in a herbicidal manner. Accordingly, one cannot merely look directly to nature to provide an immediate solution to the aforementioned herbicidal problems.

The present invention seeks to address at least some of the problems associated with such prior art. In particular it seeks to provide compositions (and their use) for horticulture and agriculture which are based primarily on naturally occurring or derived substances and which are active in their preferred area of application without the need of compounds and substances which are generally regarded as being synthetic or non-organic. However, this is not to say that synthetically produced analogues of naturally occurring substances are not within the scope of the present invention, or that simple synthetic derivatives of the naturally occurring compounds are excluded either. It is also envisaged that chemical and industrial techniques may be used to extract or render the natural materials into a usable form.

It is recognised that a distinction in agriculture between organic and no-organic compounds is, in many instances, purely semantic. In many instances there is no chemical or biological difference between a naturally sourced or naturally occurring substance, and that substance when produced synthetically. In some instances the synthetic analogue may be cleaner, purer, and more cost effective. So, for the purposes of this specification, naturally occurring shall mean substances which occur naturally in nature, rather than the manner by which they were obtained or prepared.

Further, when reference is made to derivatives of these compounds, this shall generally mean derivatives which do not substantially differ in chemical structure or properties from the naturally occurring compound. By way of example this would generally mean one or two relatively simple substituted groups on the original compound, or compounds which have added on to or reacted with functional groups on the original compound. These substituted or added groups could also be of a relatively small size (e.g. up to $C_5$ or a simple functional group) rather than being of a size or character so as to dwarf or obscure the original naturally occurring compound. Some examples, which are meant to be illustrative only rather than limiting, include soluble salts of original compounds, and the substitution or addition of simple alkyl groups etc. The main exception to this description would be esters, in which case it is desirable that the added ester group is relatively small, or comprises another naturally occurring product.

Some of the problems outlined above have been recognised in the prior art and at least the specification of WO 97/16975 considers the use of certain plant derived products. In particular, pine oils, pine alcohols, pinene, dipentene and d-limonene are advocated. Their combination with tea tree and/or eucalyptus oils, is claimed to exhibit synergy. However, preferred embodiments of this specification require distillation of natural oils and extracts to leave substantially pure terpenes of interest. This can add substantially to the expense of the composition, which is a significant factor in agriculture.

For use, the active terpenes specified in WO 97/16975 may be diluted with a suitable carrier, and a number of plant oils are listed. However, many of these oils are relatively expensive, and the application of non-volatile oils may in some circumstances be undesirable, depending upon the quantities distributed. However, in preferred embodiments of WO 97/16975 the substantially pure, distilled, compounds are applied undiluted to foliage.

The present applicant has found that direct application of the terpenes in the manner specified within WO 97/16975 may suffer from some disadvantage. For instance, the volatility of many of the components may cause them to flash-off from foliage before they are able to exhibit a herbicidal effect. This is particularly true in hot weather, and when foliage is exposed to direct sunlight. Accordingly the present invention also seeks to address this problem other than by merely increasing the quantity of active compound applied. By way of example the present invention also considers enhancing the effectiveness of active components.

The present invention also seeks to address the necessity for using highly purified, or distilled components such as advocated in WO 97/16975, or seeks at least to suggest alternatives thereto. Other aspects of the present invention nay also address other perceived shortcomings with prior art such as disclosed in WO 97/16975, such as rapidity of action.

It is therefore an object of the present invention to consider and attempt to address the foregoing problems and perceived limitations of the prior art, or at least to provide the public with a useful choice.

Further aspects and advantages of the present invention will become apparent from the ensuing description which is given by way of example only.

DISCLOSURE OF INVENTION

According to one aspect of the present invention there is provided an agricultural composition including a combination of:

a) at least one monoterpene alcohol as defined herein, and
b) a fatty acid soap and optionally including one or more carriers or diluents.

According to another aspect of the present invention there is provided an agricultural composition substantially as claimed above in which the oil is a pine oil.

According to another aspect of the present invention there is provided an agricultural composition as claimed in any one of the preceding claims in which the fatty acid soap is derived from the reaction of a tall oil with an alkali.

According to another aspect of the present invention there is provided an agricultural composition as claimed in any one of the preceding claims in which, excluding optional carriers and diluents, there is present at least 30% by weight of monoterpene alcohols as defined herein.

According to another aspect of the present invention there is provided an agricultural composition substantially as claimed above, in which there is present, excluding optional carriers and diluents, at least 55% by weight of pine oil.

According to another aspect of the present invention there is provided an agricultural composition substantially as claimed above in which there is a minimum total alcohol of 60% by weight in the pine oil.

According to another aspect of the present invention there is provided an agricultural composition substantially as claimed above, in which in addition to the pine oil there is included either or both of additional monoterpene alcohols, or plant derived oils containing same.

According to another aspect of the present invention there is provided an agricultural composition substantially as claimed above in which, excluding optional carriers or diluents, a maximum of 35% by weight of tall oil and fatty acid soaps derived therefrom are present.

According to another aspect of the present invention there is provided an agricultural composition substantially as claimed above in which, excluding optional carriers or diluents, between 12 and 25% inclusive by weight of tall oil and fatty acid soaps derived therefrom are present.

According to another aspect of the present invention there is provided an agricultural composition substantially as claimed above in which, apart from optional carriers or diluents, at least 25% by weight of fatty acid soap is present.

According to another aspect of the present invention there is provided a herbicidal composition substantially as claimed above which includes one or more of water, and water-miscible solvents.

According to another aspect of the present invention there is provided an agricultural composition substantially as claimed above which includes one or more of the following optional components: surfactants, foaming agents, emulsifiers, pesticides, compatible fungicidal agents, fertilising components.

According to another aspect of the present invention there is provided an agricultural composition substantially as claimed above which includes one or more of the following optional components: colourants, dyes, pigments.

According to another aspect of the present invention there is provided a composition, substantially as described above, which includes one or more of the following:

a terpineol, borneol, isoborneol, an anethol, a fenchol, a chavicol, a terpinene, limonene, citronellol, a pinene, camphene, camphor, a fenchone, a thujone, thymol, eucalyptol, dipentene, eugenol phellandrene, ascaridole, cedrene, carvone, or anethole.

According to another aspect of the present invention there is provided a composition, substantially as described above, also exhibiting insect repellent abilities.

According to one aspect of the present invention there is provided a composition substantially as described above, diluted with water to a concentration below a thresh-hold in which there is significant herbicidal action, for use as a pesticide or fungicide.

According to another aspect of the present invention there is provided a composition, substantially as described above, characterised such that when the composition is sprayed onto foliage a foam comprising a plurality of bubbles is created.

According to another aspect of the present invention there is provided a composition, substantially as described above, in which the foam comprises at least a monolayer of bubbles across the surface of the foliage.

According to another aspect of the present invention there is provided a composition, substantially as described above, in which the longevity of the foam is sufficient, under shaded, substantially wind and rain free conditions, is of a time during which the composition has caused visible and/or irreparable harm or damage to the plant.

According to a further aspect of the present invention there is provided a method of preparation of an agricultural composition in which fatty acid soap is prepared from the reaction of fatty acid with an alkali material, and in which there is introduced into the composition at least monoterpene alcohol.

According to a further aspect of the present invention there is provided a method substantially as described above comprising the steps of:
i) combining the fatty acid and monoterpene alcohol portions;
ii) dissolving an alkaline material in water;
iii) reacting the components of steps i) and ii).

According to a further aspect of the present invention there is provided a method substantially as described above in which the monoterpene alcohol is introduced as pine oil.

According to a further aspect of the present invention there is provided a method substantially as described above in which the fatty acid is introduced as a tall oil from pine.

According to a further aspect of the present invention there is provided a method substantially as described above comprising the steps of:
i) combining a pine tall oil with a pine oil having a total alcohol content of at least 60%, the proportion of tall oil to pine oil being within the range of 10:80 through 25:60 inclusive;
ii) dissolving a metal hydroxide in water;
iii) combining the dissolved hydroxide with the components of step (i) and allowing to react until a soap is formed;
iv) optionally including any additional components.

According to a further aspect of the present invention there is provided the use of a composition substantially as described above as a selective foliar applied herbicide, said use comprising dilution of the composition to within a range defined by observable thresholds with an upper limit being the concentration for significant or irreparable damage to desirable plants, and a lower limit being no significant damage to targeted plants.

According to a further aspect of the present invention there is provided the use substantially as described above in which the upper limit is defined by 10% or more of desirable plants being killed, and the lower limit by less than 10% or more of targeted plants being killed.

According to a further aspect of the present invention there is provided the use of a composition substantially as described above in as a pesticide or fungicide, comprising diluting the composition to below a level in which significant or irreparable damage is inflicted on desirable plants.

According to a further aspect of the present invention there is provided the use of a composition substantially as described above, as a combined herbicide and either or both pesticide or fungicide, in which the composition is applied at a concentration sufficient to inflict significant or irreparable damage to targeted plants.

According to a further aspect of the present invention there is provided the application of a composition, substantially as described above, in a manner inducing to form a foam substantially coating a surface to which it is applied with a monolayer of bubbles, whose duration is such that after 5 minutes of shaded, wind free conditions at 20° C. on a non-porous plant foliage surface at least 50% of the original foam covered surface still remains covered.

According to a further aspect of the present invention there is provided the use substantially as described above for pesticidal applications, in which the method of application maximises the production of foam or entrapped bubbles in the applied mixture.

According to a further aspect of the present invention there is provided the use of a composition substantially as described above, for pesticidal or herbicidal applications, in which the composition is applied in a manner in which at least a monolayer of bubbles are formed over at least 50% of the leaf foliage surface area to which the composition is applied.

According to a further aspect of the present invention there is provided the use substantially as described above in which application is by spray in an air stream.

According to a further aspect of the present invention there is provided the application of a composition, substantially as described above, a method for killing or severely damaging plants comprising the application of a phytoactive compound comprising at least one of a mono-cyclic monoterpene alcohol, bridged mono-cyclic monoterpene alcohol, or alcohol derivative of the foregoing, in combination with a fatty acid soap and under conditions in which the phytoactive compound is introduced to significant foliar surface area of the plant under conditions in which the phytoactive compound remains in contact with the plant's foliar and/or sub-foliar regions, for a period of time sufficient to cause cell damage and/or interfere with plant function in those regions.

According to another aspect of the present invention there is provided a method, substantially as described above, in which the phytoactive components are protected from early evaporation and kept in contact with the plant through the use of a blanketing cover of foam.

A primary role of the present invention is to control and/or eradicate plant life. Many herbicidal, compositions according to the present invention may not be phytotoxic to all plants, and/or may only be phytotoxic after repeat applications or when applied in sufficient quantity. However for the purposes of simplicity, we shall use the term 'herbicidal' to include both the eradication as well as control of at least some, if not all, known plants.

Secondary roles of the present invention include pest and insect related applications, as well as fungal related applications. By this is meant the use in the role of an insecticide as well as uses in repelling or limiting the effect of pests and insects on applied areas. This relates to the control of pests either by limiting their number through eradication or repulsion, or making the targeted areas unattractive to the pests. The term 'pests' with the specification will generally refer to insects as well as arachnids.

A similar definition applies to fungicidal aspects of the present invention.

The present invention makes use of a number of compounds which occur naturally in a number of plants. More specifically these comprise a number of monoterpenes, which will be described more fully later within this specification, and preferably monoterpene alcohols. The use of a number of these compounds have been documented in the prior art—for instance in WO 97/16975. However, as discussed previously, there are some disadvantages associated with the use of these compounds alone.

The present invention has sought to address this through the combination of such monoterpene compounds with fatty acid soaps. While it is not fully understood whether these soaps, or the vehicle in which they are presented (tall oils in preferred embodiments) there appears to be a useful advantage obtained through their inclusion. Whether observed enhanced effects over the use of straight monoterpenes is due to toxicity of the soaps, or their role in prolonging contact of monoterpene actives with the plant (this role will be described more fully later herein), or as a result of both, is not known. However, there appears to be advantage obtained through the use of particular monoterpenes (and in particular the alcohols) in combination with fatty acid soaps (and particularly those derived from tall oils).

There are a number of potentially realisable advantages associated with the various embodiments of the present invention. Among the advantages which may be exhibited in the various embodiments include very rapid action on many plants, minimal residual phytotoxic effects, low toxicity to animals, and the fact that they are primarily based on naturally occurring compounds. This represents significant and useful advantages as well as offering the public further choice in the selection of horticultural and agricultural compositions.

As indicated above, the exact mechanism of how the present invention works is not fully understood. However it is considered that plant detrimental phytoactive effects caused through the use of the present invention include dehydration and irreversible plant cell damage. This is at least partially based on observations and trials of the present invention where observable damage occurs in leafy plants in and periods of less than one hour. This is in contrast to many of the hormonal types of substances which may take several weeks to have a marked effect. It has therefore been concluded that such rapid observable manifestations of activity result from physical damage to the cell structure of the plants in at least the foliar and sub-foliar areas.

As the invention appears to cause plant damage in the leafy areas, this in turn has varying degrees of effect on plant functions associated with these areas. This includes interference with photosynthesis, transpiration and respiration. Hence, while more delicate plants appear to succumb rapidly and irreversibly from the first observable effects of dehydration and/or cell damage, the more difficult plants continue a decline due to a severe reduction in their ability to function properly. Typically the damage caused by application of the invention (over one or more applications) damages parts of the plant past the point from which the plant can recover.

In the prior art the invention of WO 97/16975 relies on the use of related compounds to the actives specified herein. However there appears to be a significant difference in the rapidity of action between the present invention (substantially faster) and the data outlined in the prior art specification. While it is difficult to draw a direct comparison between two such groups of differently trialed data, it would appear to support that the added fatty acid soap either (or both) enhances the effect of the primary active components, or acts as an active component disrupting plant function.

The rapidity of activity also supports that embodiments of the invention do not act as a phytotoxin, but rather damages the plant so it can no longer function and survive. This appears to be further supported by the negligible residual activity allowing rapid resowing and replanting of sprayed areas of land.

Preferred primary phytoactive compounds for use in the present invention comprise monoterpene alcohols, including in particular the alcohols of mono-cyclic monoterpenes, internally bridged mono-cyclic monoterpenes, and mono-cyclic monoterpenes (including both bridged and unbridged) whose mono-cyclic ring is unsaturated, as well as derivatives of the foregoing.

For simplicity of description, the term 'mono-cyclic monoterpene' shall when used within this specification, unless otherwise specified, refer to both bridged and unbridged mono-cyclic monoterpenes—the bridge being an internal bridge across the ring, as well as mono-cyclic monoterpenes whose mono-cyclic ring is unsaturated.

Less preferred primary phytoactives for use in the present invention include the aldehydes and ketones of mono-cyclic monoterpenes (as defined above). However the preference is for the use of monoterpene alcohols and when the aldehydes or ketones are used the preference is for the use as a secondary active component in addition to monoterpene alcohols as the primary active component.

Also of interest as phytoactive compounds in the present invention are derivatives of the foregoing—a discussion of what is regarded as being derivatives within the scope of the present invention has previously been given.

There are a number of compounds which fall within the above group of phytoactive compounds. As can be readily ascertained, these are based on monoterpene compounds which comprise a broad group of compounds derived from the bio-synthesis of (typically two) $C_5$ (typically isopentene) units. The resulting monoterpene compounds are typically $C_{10}$ compounds and may be linear, bridged, or cyclic.

Examples of some preferred phytoactive compounds falling within the above grouping include the borneol family of compounds (representative of bridged cyclic monoterpenes), the terpinene families (including the various terpinenes which are representative of monocyclic monoterpenes in which there is a degree of unsaturation in the monocyclic ring), terpineols (which are representative of monocyclic monoterpene alcohols). There are also a number of other phytoactive compounds falling within the above definitions. These include, but are not restricted to, compounds in families including: the terpineols, the borneols, the isoborneols, the anethols, the fenchols, the limonene family, the pinene family, the camphene family, the thujol family, dipentene, the eugenol family of compounds, the phellandrene family, and the carvacrols. In the context of the group of (primary and secondary) phytoactive compounds, the above groups and families should generally be taken to mean the alcohols, ketones, and aldehydes but may also include cyclic compounds bridged by an oxygen atom.

In practice, embodiments of the present invention may comprise only one of the group of phytoactive substances. However, as it is envisaged that most of these will be derived from natural sources, it is envisaged that there will commonly be present more than one of these phytoactive components. This may be economically sensible as well, as purification of naturally derived products to exclude other components present is often both unnecessary and not cost effective. In addition—and it should be appreciated that the mechanisms of the invention are not fully understood—it is considered that while the actions of the various phytoactive compounds are equivalent in action they are not necessarily identical. There may be some variation in the activity of different members of this group, and this will also depend upon a number of other factors including the species of plant to which it is applied, the conditions under which it is applied etc. Where a non-selective herbicide is desirable, there may be some advantage in including two or more of the phytoactive components in a composition.

Similarly, there may be some advantage in including a number of other naturally occurring components in compositions according to the present invention. Envisaged are non-monoterpene compounds which are nevertheless very related to the monoterpenes and often occur naturally in some plants in conjunction with members of the phytoactive group. Examples of some of these additional components include the chavicol family, the citronellol family, and ascaridole family of compounds.

In a preferred embodiment of the present invention, the oil of an evergreen tree, rich in preferred phyto-active components, forms the basis for introducing the active compounds into the composition. Preferred evergreen trees are conifers, and for commercial reasons pine is preferred. The preference is to use oils which are rich in monoterpene alcohols (as defined herein) and preferably having a total alcohol content of at least 50%, more preferably 60%, and ideally at least 80% by weight.

By 'total alcohol content' is meant the percentage, by weight, of the material being considered which comprises compounds which are alcohols.

Preferred oils for introducing monoterpene compounds, according to the present invention, are pine oils. Pine oils vary in composition according to a number of factors. Preferred pine oils for use with the present invention are those having a total alcohol content of at least 60%, and more preferably at least 80%. It is also preferable that the majority of these alcohols comprise terpineol or pinene. A typical assay of a suitable pine oil is given in the examples.

The total alcohol content of the pine oil, or other components used for introducing monoterpene alcohols, will have a bearing on the required percentage of the oil (or component) in a concentrate formulation. Typically for a concentrate, to be diluted such as outlined in the ensuing examples, a minimum monoterpene alcohol content of at least 25% is desirable. More preferably 40%, and ideally at least 50% in the finished concentrate. This is assuming a concentrate possessing a maximum of 10% of diluents and carriers. Calculations may be performed to find equivalent desirable levels for compositions with other carrier/diluent levels.

The use of secondary active compounds have already been noted. It is envisaged that such secondary actives may be used to supplement monoterpene alcohol levels, though it is preferred that at least the minimum levels of monoterpene alcohols outlined above are present. However, a composition having only a 25% level of monoterpene alcohol will be more effective if there is, for instance, another 25% of monotone aldehyde or ketone also present as a secondary component as opposed to carriers, diluents, or non-active components.

It is also noted that commercially available 'natural' pine oils are often rich in sulphur compounds as a consequence of the methods by which they are extracted. The raw products may be further refined to remove these sulphur compounds. Either form may be used in embodiments of the present invention. The choice will often be a compromise between cost, and the acceptability of one form over the other in the market place.

Present in embodiments of the present invention are enhancing agents able to enhance the activity of the preferred active components. In the preferred embodiments of the applicant, these enhancers comprise fatty acid soaps. These components appear to enhance the activity of the primary active components (i.e. the monoterpene compounds) as well as enhancing the rapidity of their action. Yet further, this also appear to extend the usefulness of compositions according to the present invention for pesticidal and anti-fungal roles.

Fatty acid soaps used generally comprise the salt of a fatty acid with a suitable cation—usually sodium or potassium. For economy, most fatty acid soaps in the present invention will have sodium as the cation, while the fatty acid will often be predominantly based on an alkyl in the $C_{14}$–$C_{22}$ range.

The source of the fatty acid may vary. This may comprise compositions materials rich in fatty acids and which have been derived from natural materials. The preference is to use plant derived materials. Preferred embodiments of the present invention, and particularly those using pine oil, utilise tall oil as the fatty acid source. This is typically reacted with a suitably alkaline agent, typically sodium hydroxide, to produce a soap.

As mentioned previously it is considered that the full nature of the role of the fatty acid is not understood. It is anticipated that part of the effectiveness of the present invention may result at least partially from the ability of the fatty acid soap to encourage a layer of bubbles or foam which inhibit evaporation of the primary active components (the monoterpene compounds) from foliage. It is also considered that the fatty acid soaps may also be active in disrupting plant function, disrupting cellular or macro cellular processes in structures etc. The part hydrophilic and lipophilic nature of the soaps may also assist in enhancing the effectiveness of the primary active components, as well as interfering with the processes and structure of the plant.

It is also anticipated that other components in reagents such as tall oil may also be active in disrupting plant function. This may be one reason why the pine oil and tall oil based preferred embodiments of the present invention are especially effective.

The role of the carrier and diluents which are optionally used in conjunction with the present invention (they may not be present, or present only in limited amounts, in concentrates but are generally included in ready to use compositions) needs to be considered. The use of a suitable carrier or diluent, and in particular water, may extend beyond the mere use as a diluting agent for distribution of the other components. This will be described further below.

Hence, while it is envisaged that the above compounds will have an adverse effect upon plant material to which it is applied, application of the concentrated substances is generally economically impractical and expensive. For this reason it is generally desirable to include a suitable carrier for when the compositions are to be applied. While this could conceivably include suitable organic solvents, the difficulty in working with these carriers in an agricultural environment will generally preclude their use. Such difficulties include flammability and explosion dangers, as well as regulations governing the release of solvents into the environment. For this reason, preferred embodiments of the present invention will rely on water as the preferred carrier.

Another composition involves the conditions upon which the spray is generally applied. In many environment volatile organic substances will flash off relatively quickly. If this happens too quickly, then the applied phytoactive components may be incapable of establishing the intimate contact with plant material required to result in plant damage. For this reason it is desirable to have a spraying composition which will promote or encourage intimate contact between the phytoactive components and the plants to which the composition is applied.

The use of water as a carrier goes some way towards solving this problem as water is not particularly volatile in comparison with many organic solvents and compound. In addition the bulk of the water may have a slight cooling effect on the foliage so that any applied organic compounds are less likely to evaporate off. Further, water (though this is also true of some organic solvents) will readily migrate into the plant surface and may help carry with it any dispersed phytoactive components, particularly in combination with the presence of soaps, and optionally included additional components such as surfactants.

While such additional components may include surfactants and wetting agents, many wetting agents and surfactants are of synthetic origin and may not be permissible for organic farming methods. Consequently their use may preclude the present invention from being used in an area for which it was at least ally developed. Secondly, many surfactants and wetting agents alone (in lieu of the fatty acid soaps) will not necessarily provide another advantage of preferred embodiments of the present invention. This further advantage comprises the ability, under ideal spraying conditions, to a least partially insulate the phytoactive components from the environment while they have a chance to work on the plant surface to which they are applied. Quite simply this can be achieved by the provision of a protective layer against rapid loss or evaporation of the phytoactive components and to also direct their action towards the plant. In practice this is found to be accomplished by the use of compositions which produce foam when sprayed onto the plant surface. In the present invention, the fatty acid soaps afford the foaming properties, though these may be enhanced by other commercially used and known foaming agents, or substances which increase the stability of foams or bubbles.

The insulating foam produced upon application need not be a substantial foam, but may merely comprise a monolayer of bubbles over the surface to which the composition is applied. This need not be the entire surface though ideally should cover at least 50% of the surface area, and more preferably at least 60%.

The probility of the foam or bubble structure is another consideration. Ideally, such a foam would be long lived though in practice may have a half-life of the order of 3–5 minutes. In some instances shorter lived foams are also acceptable though a general preference would typically be foams whose duration is as follows:

preferably, under shaded wind-free conditions at 20° C., applied to a broad-leafed plant surface which is not especially porous, at least 50% of the original surface area covered by foam or bubbles will still remain after 2 minutes;

more preferably, under the above conditions, the same proportion of surface area should still remain covered by foam or bubbles after 5 minutes, and even more preferably, the same proportion of surface will be covered after to 10 minutes.

A particular test which may be applied is given in the detailed examples hereafter.

It should be envisaged however that different conditions will have an influence upon what is acceptable in practice. Under higher ambient temperatures, the action of the phytoactive components may be quicker and absorption into the plant may also be quicker. Under these conditions foams which last a lesser period of time may be acceptable.

Similarly it is envisaged that as the applied composition migrates into the plant structure, the ability to maintain a foam on the surface will also be lessened. In many instances, destruction of the foam or bubble structure is a result of the applied composition having the desired effects and entering into the plant. Under such conditions, it would no longer be necessary to maintain a protective foam layer as the components will have already performed a substantial proportion of their job. It is envisaged that many broad-leafed plants will fall into this category while other plants, and especially those having waxy surfaces slowing penetration of the phytoactive components, may require the foam/bubble covering to protect it from the environment for greater periods of time. These considerations should be borne in mind when preparing compositions of the present invention, and also in the preparation of their final spray compositions. However it is noted that tall oils are particularly effective in dissolving waxy substances and thus embodiments including tall oil fractions will exhibit increased effectiveness against plants having waxy leaves or foliar surfaces.

It is envisaged that there may be different embodiments destined for different types of application e.g. broad-leafed v. woody or difficult plants. Here the portion of components may vary to address any particular problems associated with that type of plant or grouping.

While foams may be produced by a number of different effects, it has been found in trials by the applicant that a useful foam structure may be achieved through the inclusion of fatty acid soaps with the phytoactive components. Common sources of fatty acids including those derived from plants (e.g. some tallol'or tall oil formulations) represent a useful source of fatty acids for use in the present invention. These are usually reacted with a suitable alkaline material to form a soap for use in compositions of the present invention.

The use of fatty acids and their soaps appears to give a foam structure, particularly when combined with water as a diluent and applied with an air carrier, contributing to many of the advantages discussed before. However, it also appears that the use of these fatty acids and their soaps, as well as satisfying criteria for the use of organic compounds (insofar as the term organic is used in relation to agriculture), enhance the activity of the phytoactive components. As has been mentioned previously, the exact mechanisms of the present invention are not fully understood though initial trials indicate that the combination of the phytoactive components with fatty acids and their soaps yields a highly effective herbicide with a very rapid effect (see also examples later herein).

Accordingly, preferred embodiments of the present invention comprise a combination of the preferred phytoactive components with substances able to produce a covering foam, but most preferably where the substances include or are based on fatty acids. At this stage there is no indication that any particular fatty acid is preferable to others though there may be some benefit in using fatty acids derived from plants, which represent one major commercial source of fatty acids, and particularly using tall oil.

Various compositions may also include a number of additional optional components. These may include active compounds which perform a particular role. These may merely rely on the compositions of the present invention as a carrier for their distribution, or may actively participate in how the present invention works. In the former category, these may include additional insecticides, fungicides, or other agricultural chemicals which act separately from the present invention. It is anticipated that their inclusion is primarily to avoid the user making two spray applications to plant material, though it is also envisaged that there may be some additional advantages which result from the combined use.

In the second class are components which participate in the working of the invention, or its usefulness. This may include surfactants and wetting agents as mentioned above. In addition this may include additional foam enhancing agents. These may be agents which produce a foaming effect, or may alternatively prolong the life of any bubbles or foam produced in the present invention. A number of such agents are known commercially in these roles and may be employed in the present invention, providing the composition still conforms with user requirements (e.g. the presence or absence of non-organic materials).

Other components which may be optionally added include pigments and colourants. This may simply for the role of enhancing the aesthetic appeal of the product (or for practical reasons such as to distinguish it from other substances. In addition it may serve a role as a marking for areas of foliage which have been sprayed, which would be particularly useful for aerial application of the present invention. Other optional components commonly used within the agricultural industry may also be considered for inclusion in the present invention.

Also included within the scope of the present invention are uses of the compositions. In most cases the main role of these compositions will be as a herbicide. This will typically be as a non-selective herbicide, and providing a suitable concentration is used, a useful non-selective herbicidal action against most plants can be achieved.

Methods of use may include repeat applications. This will tend to emphasise the effects of earlier sprays and may be used to address plant growth which missed the first spraying pass, or which survived that pass.

The present invention may also be used in a selective manner. Trials suggest that the present invention is most effective against broad leaf plants. Accordingly, there is application for the present invention as a selective broad leaf herbicide. Such uses will rely, as for most selective herbicides, upon the greater effect of the herbicide on some plants than others.

Compositions used for selective applications will usually be diluted to within a particular range of dilutions. While this will depend also upon the application rate, a typical dilution will be selected to fall within a range of threshold values falling below the point where desirable plants are affected adversely, but above the point where there is minimal harm to targeted plants. While user acceptability may differ, it is typically envisaged that the compositions will be applied in a manner such that no more than 10% of desirable plants are irreparably or significantly damaged and impaired. Similarly, there should be at least 10% mortality rate in targeted plants. In some instances either or both of these limits may be increased or decreased, depending upon acceptability. However, it should also be considered that a lower degree of mortality may be acceptable for when the composition is being used in manner to slow the growth of targeted plants so as to provide desirable plants with a competitive advantage.

Typical selective herbicidal uses of the present invention may include lawns, weed control between trees and saplings (e.g. in forestry, orchard, and plantation) as well as weed control between crops. In some of these applications a greater degree of selectivity may be achieved by limiting application of the herbicidal composition to the vicinity of the targeted plants. This will minimise the impact of the composition on desirable plants, as well as reducing wastage of composition. Because the effectiveness of the present invention appears to be greatest when applied to foliage, it may find use for controlling weeds in between crops, as well as in forestry and plantations where compositions sprayed onto the basal area of trunks and stems of desirable plants may have a minimal effect compared with the control of the targeted weeds.

It has also been noted that the present invention can also exhibit pesticidal and fungicidal activity. Again in these applications a dilution and rate of application is generally chosen to avoid damage to desirable plants but to provide a useful level of pest and fungal control. In particular it has been noted that the foaming nature of the present invention is particularly effective against sucking and chewing pests. As for plant foliage, the layer of bubbles/foam appears to trap the active components over the body of the pest until such time as it has exhibited a toxic effect. In addition, there may be suffocation of the pest which literally drowns in the foam.

Finally, it is envisaged that the present invention may be used in a combined role where it may act as a herbicide as well as either or both a fungicide or pesticide. In such instances, lesser dilutions may be used. Particular uses may include spraying between other desirable plants to control weeds. The anti-fungal properties can delay decomposition such that the affected plant material tends to dry first. Such material tends to more slowly break down and in the interim period tends to act as an effective mulch. This application may be particularly useful in drier areas.

BEST MODES FOR CARRYING OUT THE INVENTION

The following examples are given by way of example only. They are not meant to be limiting but merely demonstrative of some various ways by which the present invention may be implemented, prepared or formulated.

EXAMPLE 1

This example is direct less to a particular formulation according to the present invention but more to a method by which the effectiveness of various embodiments may be gauged. The following is a test which can be used to determine the duration of a foam structure. It may be used to determine preferred useful embodiments of the present invention, as well as representing one standard by which the foam structure of different embodiments may be compared.

The test comprises the spray application of a spraying embodiment of the present invention. This spraying embodiment represents the diluted ready to use form of a composition according to the present invention. Accordingly, these tests may be used not only to assist in the preparation of different formulations of the present invention, but also to determine the preferred dilution ratios and carrier proportions.

The spraying composition is sprayed at a pressure of 35 psi air pressure through a solid cone 0.5 mm orifice with a turbulator. The ideal surface is one representative of a broad-leafed plant. By way of example this may be a dandelion or hawk-bit leaf which is not under any particular stress. Other plants may include wild ginger, dock, or scotch thistle. Preferably an average obtained for a number of different plants would be obtained.

The test should be performed at an ambient temperature of 20° C. and protected from both wind and direct sunlight. The leaf surface should be dry and dust free.

After spray application, at least 60% of the surface area to which the composition was applied should be covered with at least a monolayer of bubbles. The time should be recorded for when a drop to 50% of this original area covered by foam/bubbles occurs—e.g. if the initial coverage was 70%, then time will be until coverage drops to 35%.

least preferably, this period should be 2 minutes or grater. More preferably this period should be 5 minutes or greater. Ideally, this period would be 10 minutes or greater.

An alternative measure is when physical damage to the leaf becomes visible, though this can be relatively subjective.

EXAMPLE 2

This example represents a typical scenario for the application of spraying compositions according to the present invention. This is particularly relevant to compositions such as described in example 5.

The composition, suitably diluted, was sprayed at a pressure of around 35 psi through a solid cone 0.5 mm orifice with a turbulator. The composition was applied on a sunny day at 25° C. ambient temperature. There was no wind.

The composition was applied to a mixed foliage comprising typical pasture. In this example the pasture comprised both grasses and broad-leaves such as dandelion, which were dry of surface water and free of dust. The result was a light foam having bubbles of approximately 1–2 mm diameter, which were white in colour and adhered to the foliage. The coverage was visible to the naked eye, which may be of advantage in many applications.

Under these conditions, preferred compositions of the invention will disappear after approximately 10 minutes of application leaving a visible discoloration of the foliage to a darker green. This darker green, which generally increases in darkness until browning off occurs (with visible dehydration) is indicative of stress and damage to the plant through the application of the composition.

EXAMPLE 3

This example represents the typical time frames for significant and visible stress or damage to the plants according to use outlined in Example 2.

TABLE 1

| Item | Time frame for significant visible damage or adverse effects |
|---|---|
| Buttercup | 1 hour |
| Ragwort | 2 hours |
| Short grasses | 1 hour |
| Nightshade | 1 hour |
| Dock | 2 hours |
| Dandelion | 1 hour |
| Scotch Thistle | 24 hours |
| Gorse | 24 hours |
| Wild Ginger | 10 hours |

This table should be used primarily for comparative purposes rather than as a source of empirical data. Actual time frames will vary according to the strength of the applied composition, the saturation, the conditions under which the composition is applied, the health of the plant, the size and environmental conditions for the plant, etc.

It is noted also that some of the more virile species such as gorse will react first by dropping the head of each stalk, followed by a colour change to lighter green but all within the specified time frame above. However, it may be from between 3–7 days (on the above time scale) after spraying the gorse before it will have turned brown and be dry enough to burn off. Other species such as wild ginger will sag quickly and fall over as it subsequently dries out over the next two or three weeks.

The residues which may remain in the plant from embodiments of the present invention are generally harmless to subsequent plant growth. In some respects they may be likened to contact poisons when under certain preferred conditions. While some residue will main in the decaying plant matter, the phytoactive components generally only adversely affect plants when they are able to have a localised effect on plants. During spray applications this localised effect is on the entire exposed surface of the plant.

Typically it has been observed that the foliage on the targeted weed is in the same condition as if it had been pulled from the ground and allowed to decompose. It has been found to be a useful mulch that can be left to decompose or cultivated back into the soil as many of the components of the present invention are naturally occurring products derived from plants, most plants will have no adverse effects from minor amounts of residue which may remain in the soil or mulched plant matter.

EXAMPLE 4

The following represent some generalised examples of compositions according to the present invention. There are a large number of embodiments which may be formulated within the scope of the present invention as defined herein. The following represent just a few examples which are meant to be illustrative only.

EXAMPLE 4a

This represents a concentrate which may be subsequently diluted with water before application;

| Percent by volume | Component |
|---|---|
| 50–95% | Pine Oil |
| 0–45% | One or more oils from an evergreen tree preferably coniferous. |
| 5–50% | Fatty acid of which at least 10% is present in the form of a soap of a fatty acid. |
| To a total of 100% by volume. | |

EXAMPLE 4b

This is another concentrate:

| Percent by volume | Component |
|---|---|
| 30–90% | Oil from a coniferous evergreen including pine, cedar, fir; |
| 0–60% | Terpineol, methyl chavicol, borneol, isoborneol, pinene, cedrene, camphene, terpinene-1-ol, and/or terpinene-4-ol. |
| 0–30% | Oil of a non-coniferous evergreen tree such as Eucalyptus; |
| 3–50% | One or more alcohols, aldehydes, or ketones of one or more of the following families or groups of compounds: anethol, chavicol, limonene, citronellol, camphene, camphor, fenchone, thujone, phellandrene, ascaridole, and carvone. |
| 3–50% | Fatty acids, preferably plant based and of which at least 10% is present in the form of a soap of the fatty acid, and wherein at least 3% by weight of the total undiluted composition comprises fatty acid soap. |
| To a total of 100% by volume. | |

EXAMPLE 4c

| Percent by volume | Component |
|---|---|
| 50–90% | Product # OI 100 manufactured by Akzo Nobel of Tauranga, New Zealand; |
| 10–50% | Fatty acid including one or more of palmitic acid, stearic acid, oleic acid, linoleic acid, pimaric acid, sandarocopinaric acid, palustric acid, levopimaric acid, abietic acid, dehydroabietic acid, and neoabietic acid, and wherein the fatty acid has been combined in with an alkaline metal (preferably sodium hydroxide) solution. |

| Percent by volume | Component |
|---|---|
| To a total of 100% by volume. | |

A preferred concentration of alkali metal hydroxide is 25–50% w/v.

The list of fatty acids of this example may also be used as representative fatty acids for the other examples herein.

EXAMPLE 5

EXAMPLE 5a

A preferred embodiment of the present invention comprises from 55–95% natural or refined pine oil. Preferably the pine oil has a total alcohol content of at least 60%. Pine oil from the U.S.A. has a typical total alcohol content of around 65%, while New Zealand Pine oil has a typical 85% content.

The US pine oil is effective in herbicidal compositions though the maximum dilution of such concentrates may be lessened if a useful result is to be achieved.

The preference is for the use of New Zealand pine oils having an 85% alcohol content. Trials and dilutions outlined in this specification have been based on the use of New Zealand pine oil. In particular the pine oils obtained from Eka Nobel and sold under the labels PINECHEM 530, PINECHEM 550, and PINECHEM 317 have been used.

The fatty acid/tall oil combination has been prepared by the reaction of a tall oil with sodium or potassium hydroxide. The tall oil should also be derived primarily from pine, and may be obtained from Eka Nobel, also of Tauranga, New Zealand.

A preferred ratio of tall oil to pine oil is within the range 10:80 through 25:60 inclusive. A specific formulation follows:

EXAMPLE 5b

Within a tolerance of 2% the formulation comprises, by weight:

| | |
|---|---|
| Tall oil/fatty acid combination: | 20% |
| Water: | 10% |
| Pine oil (80% or greater alcohol content): | 70%. |

This represents a concentrate which may be subsequently diluted for use. Typical dilution ranges are as per Example 6.

EXAMPLE 5c

A method of preparation of the compositions of Examples 5a and 5b is as follows. The same method may also be applied to the compositions of other examples given herein.

The pine oil and tall oil components are combined and blended.

A solution of sodium hydroxide is prepared in the proportion of 25% NaOH to 75% H$_2$O. This solution is slowly added to the pine oils with tall oil combination. Typically 1 part of hydroxide solution is combined with 9 parts of pine/tall oil blend.

As per normal practice, the hydroxide solution is preferentially added to the greater volume of oils. Some heat will be produced through the dilution of the hydroxide solution which will promote the reaction to form soaps with fatty acids present in the tall oil.

Care should be taken to ensure adequate mixing during the addition of the hydroxide. Failure to do so may result in a substantially non-homogenous solution with lumps of soaps distributed in localised pockets throughout the resulting product. This is undesirable and may require additional blending to produce a substantially homogenous product (phase considerations aside) at the end of the process.

While additional components may be added prior to the addition of the hydroxide solution, they will be typically added after the main soap forming reaction.

The result is a concentrate which may be diluted before use. The preferred diluent is water to assist in foam formation. As a broad spectrum control system, the concentrate may be diluted 1:7 (by volume) with water. For woody and mature species a 1:5 dilution ratio may be used. Weaker spraying compositions based on a 1:9 dilution ratio may be used in some instances.

Reference has been made to some products available from the company Eka Nobel, from their Tauranga, New Zealand branch. A range of different products are available which may find use in the present invention, though specific grades and fractions of pine oils etc. have been identified which have been tested and found to be suitable for use in the present invention.

Each of these products are prepared to be substantially consistent in their composition. While it is anticipated that manufacturer's specifications are often subject to change, reference can be made to manufacturer's data sheets detailing specifications of products available in 1998/1999.

For the assistance of the reader, primary components in the preferred pine oils specified above comprise:

| | |
|---|---|
| alpha terpineol: | around 50% |
| Beta terpineol: | around 13–15% |
| Borneol: | around 8–9% |
| Terpinene-4-ol: | around 5% |
| Other terpene alcohols: | around 5–8% |
| Other components: | to a total of 100%. |

By way of example, a tall oil rich in fatty acids is the product PINECHEM 317. A typical composition of a product of this type is:

| | |
|---|---|
| Oleic acid: | around 25–30% |
| Linoleic acid: | around 20% |
| Stearic and palmitic acids: | around 1–2% |
| Pimaric acid: | around 9–10%. |

Fatty acids of those specified above: 25–30%.

Various other acids and components to a total of 100%.

The above lists are intended to be illustrative only. Oils (including oils other than those based on pine) and fatty acid sources with significant differently compositions are also envisaged to fall within the scope of the present invention. However, these particular component distributions exist in compositions which the applicant has found to be particularly useful.

EXAMPLE 6

The embodiments of the present invention may also be put to other uses. This includes use as a germicide, or bactericide (many of the phytoactive components also have germicidal and/or bactericidal effects). While this may be a primary role of the compositions, it is envisaged that it will be a supplementary or secondary advantage of the present invention.

It may also find a role as a fungicide or in the control of fungi.

Finally, it also has some insecticidal capabilities AND/OR may act as a repellent. Some of the phytoactive components and/or other preferred added components, are unattractive to insects and can act as either an insecticide or more commonly as a repellent to insect infestation.

Some preliminary tests using embodiments of the present invention (as per Example 2 and at the dilutions thereof) had a noticeable effect on insects within the following time frames:

TABLE 2

| Insect | Time frame for significant visible damage or adverse effects |
|---|---|
| Aphids | Less than 1 minute |
| Black Beetles | 2 minutes |
| Crickets | 2 minutes |
| Green Shield bug | 2 minutes |
| Ants | 2 minutes |
| Wasps/Hornets | 4 minutes. |

EXAMPLE 7

The following characteristics are given in relation to the use of compositions such as given in Examples 2 and 5:

in the case of plant species which grow from a strong root structure, re-application to re-growth may be required. This will eventually stress the plant permanently resulting in its eradication;

creeping varieties such as Kikuyu and Couch will be controlled when sprayed however, if the stem is thick a timed re-application will be necessary;

heavily rooted plants such as Paspallum with thick seed stems appear to need timed re-application even though their leaf foliage dehydrates almost straight away. However after re-application they will be permanently stressed and eradicated;

the above examples are also subject to the season. Any grow back after initial application is reduced during the plant's growing season while in the dormant season re-treatment may be unnecessary due to the reduced activity of the plant during that period;

eradication of pests in the pasture and foliage is evident and appears effective across a wide range of species. When treating weeds it is inevitable that pests will also be sprayed. These appear to die or quickly move from the affected areas and may then die;

colour changes and wilting will occur sometimes within an hour;

most compositions are bio-degradable and/or evaporate their main components. For the concentrate, a typical expected breakdown period of around 60% bio-degradation or other removal within 28 days. However, use of the invention involves a diluted form. Preliminary trails suggest that for a 1:5 dilution (relatively strong spraying composition) the biodegradation/elimination period is much less and in favourable circumstances may even be measured in hours.

it appears that the phytoactive components do not leach into surrounding plants or the soil in any appreciable or significant amount;

the pleasant odour associated with many of the phytoactive components is a characteristic after spraying;

the preferred composition are generally non-toxic or of very low toxicity to humans and other warm blooded animals;

the included fatty acid soaps afford good penetration and wetting action in most applications;

the foam cover in preferred embodiments enhances action of the active components;

preferred embodiments leave a visible indication of where they have been applied;

at least sore herbicidal, insecticidal germicidal, and fungicidal activity may all be obtained using the one composition.

EXAMPLE 8

The present invention may also be used in the role of a selective herbicide. This use will depend primarily on the method of use of the invention rather than solely on the composition. However, it is anticipated that different embodiments of the present invention will have different effects on different plants. Accordingly, particular embodiments which exhibit greater or lesser effects against particular plants will preferentially be used in selective type applications.

It is impractical to provide data for all available plants and often environmental factors will also affect the exact results obtained. While a certain degree of latitude exists for herbicidal applications (for instance it does not matter whether the exact amount, or twice as much, herbicide is used) there is a lesser degree of latitude for selective type operations. Accordingly it is envisaged that prior to use the user will perform some brief tests to optimise the dilutions and application rate appropriate for their particular use.

EXAMPLE 8a

As a guide, a small area of selected plants representing both targeted and desirable plants is chosen. These should ideally be selected in an environment which closely matches the environment to which the herbicide is intended to be applied in a selective manner.

A range of dilutions of herbicide are prepared, and typically the strongest of these will be at a dilution less than that typically used for general non-selective herbicidal application. By way of example the strongest solution will typically be 1:11 with water.

The differing concentration are applied and the observed results evaluated for the best ratio between target weed control, and minimum desired plant damage.

EXAMPLE 8b

A specific example for broad leaf control and lawn may be as follows. An area of lawn is divided into squares of perhaps 0.5 metres×0.5 metres. The lawn should be relatively uniform in terms of both the distribution of targeted weeds and the species of grass which has been sown. If necessary the size of each test area may be varied to ensure a more representative sample area.

A range of different dilutions are applied, one to each sample square. As the effects are generally quite rapid, the sample plots can be evaluated after two hours, though ideally, the sample plot should be re-checked after a greater period of time e.g. 1–3 days, to determine whether there are any longer term effects.

The dilution chosen will be one which represents a reasonable compromise between control of broad leaf weeds but minimal damage to the grass.

It is also noted that different species of pass and weeds, may vary significantly in their sensitivity to the present invention. Accordingly the present invention may not be able to be used in such a selective type manner in all instances.

EXAMPLE 9

While herbicidal embodiments of the present invention will also tend to exhibit some pesticidal and fungicidal control, there are instances where pesticidal and fungicidal effects are desired over herbicidal effects. This may include the control of insects, pests, and fungi on desirable plants.

Again, because there is only a small degree of latitude in such applications of the invention, and because the sensitivity of different plants varies so much, it is desirable that a series of tests similar to that of the preceding example are performed. However, in this case the evaluation of the trial results will be to determine the maximum possible concentration of composition which may be applied without significant damage to the plant(s).

Insect control can be enhanced in many instances by increasing the foaming effect—not only in terms of the amount of foam produced, but also the longevity of the foam. Accordingly, the addition of commercial known and used foaming agents, and bubble stabilising components, may also be considered. Manufacturer's data sheets, and some minimal trial and experimentation by the user will be able to determine which such commercially available components are most effective for the intended application. Again if it is intended that the composition is to be used according to organic farming methods, then some consideration may need to be given as to the acceptability of any added components.

Aspects of the present invention have been described by way of example only and it should be appreciated that modifications and additions may be made thereto without departing from the scope thereof as defined in the appended claims.

What is claimed is:

1. An agricultural composition comprising:
    a) a monoterpene alcohol portion comprising a pine oil with an alcohol content of at least 60% by weight;
    b) a fatty acid soap from the combination of either or both tall oil, or a fatty acid compound, with an alkali metal compound, wherein said agricultural composition comprises sufficient fatty acid soap and/or sufficient foam enhancing agent to allow the composition to be applied as, or to produce, a foam having at least a surface monolayer of bubbles during use; and
    c) a fertilizer.

2. An agricultural composition as claimed in claim 1, wherein the monoterpene alcohol portion comprises pine oil having an alcohol content of at least 80%.

3. An agricultural composition as claimed in claim 1, wherein the fatty acid soap is derived substantially entirely from tall oil, and wherein the ratio of tall oil to pine oil used in preparing the composition is within the range of 10:80 to 25:60 by weight.

4. An agricultural composition as claimed in claim 1, wherein the monoterpene alcohol portion and the fatty acid soap comprise at least 55% by weight pine oil.

5. An agricultural composition as claimed in claim 1, wherein the monoterpene alcohol portion further comprises at least one monoterpene alcohol or plant derived oil containing at least one monoterpene alcohol.

6. An agricultural composition as claimed in claim 5 wherein the at least one monoterpene alcohol or plant derived oil containing at least one monoterpene alcohol is selected from the group consisting of pinenes, terpineols, borneols, isoborneols, eucalyptus oil, citronellol, liminol, and oils from the citrus family.

7. An agricultural composition as claimed in claim 1, further comprising at least one member from the group consisting of mono-cyclic monoterpene aldehydes, mono-cyclic monoterpene ketones, bridged mono-cyclic monoterpene aldehydes, bridged mono-cyclic monoterpene ketones, internally bridged mono-cyclic monoterpenes, unbridged mono-cyclic monoterpenes, anethols, fenchols, members of the limonene family, members of the camphene family, members of the thujol family, dipentes, members of the eugenol family, members of the phellandrene family, and cavracols, and simple substituted derivatives of the foregoing.

8. An agricultural composition as claimed in claim 1, wherein the monoterpene alcohol portion and the fatty acid soaps comprise a maximum of 35% by weight of tall oil and fatty acid soaps.

9. An agricultural composition as claimed in claim 8 wherein the monoterpene alcohol portion and the fatty acid soaps comprise between 12 and 25% by weight tall oil and fatty acid soaps derived therefrom.

10. An agricultural composition as claimed in claim 1, wherein the amount of fatty acid soap present is sufficient to produce at least monolayer of foam covering at least 60% of foliage surface area to which the agricultural composition is applied.

11. An agricultural composition as claimed in claim 1, further comprising at least one carrier or diluent selected from the group consisting of water and water-miscible solvents.

12. An agricultural composition as claimed in claim 1, further comprising at least one component selected from the group consisting of surfactants, foaming agents, emulsifiers, pesticides, and fertilizing components.

13. A ready to use composition comprising an agricultural composition as claimed in claim 1, wherein the agricultural composition is diluted up to 1:9 with diluent comprising water.

14. A composition of claim 1, diluted with water to a concentration below a thresh-hold in which there is significant herbicidal action, wherein the diluted composition is for use as a pesticide.

15. The agricultural composition of claim 1, further comprising a foam enhancing agent.

16. The agricultural composition of claim 1, further comprising at least one carrier or diluent.

17. An agricultural composition as claimed in claim 1, further comprising at least one compatible fungicidal agent.

18. A composition of claim 1, diluted with water to a concentration below a threshold in which there is significant herbicidal action, wherein the diluted composition is for use as a fungicide.

19. A method of preparation of an agricultural composition comprising:
   a) combining a monoterpene alcohol portion comprising a pine oil with an alcohol content of at least 60% by weight with at least one tall oil, and/or at least one fatty acid compound and at least one fertilizer;
   b) dissolving an alkaline material in water; and
   c) reacting the components of step a) with the components of step b).

20. The method of claim 19, further comprising adding in step a) at least one material selected from the group consisting of plant derived monoterpene alcohols, plant derived oils containing monoterpene alcohols, mono-cyclic monoterpene aldehydes, mono-cyclic monoterpene ketones, bridged mono-cyclic monoterpene aldehydes, bridged mono-cyclic monoterpene ketones, internally bridged mono-cyclic monoterpenes, unbridged mono-cyclic monoterpenes, and simple substituted derivatives of the foregoing.

21. The method of claim 19, wherein the pine oil has a total alcohol content of at least 80% by weight.

22. The method of claim 19 wherein, apart from water, at least 55% by weight of pine oil is present in steps a) and c).

23. The method of claim 19 comprising the steps of:
   i) combining a pine tall oil with a pine oil having a total alcohol content of at least 60%, wherein the proportion of tall oil to pine oil is within the range of 10:80 through 25:60 inclusive;
   ii) dissolving a metal hydroxide in water; and
   iii) combining the dissolved hydroxide with the components of step (i) and allowing to react until a soap is formed.

24. The method of claim 23, further comprising adding optional components.

25. A composition prepared according to the method of claim 23.

26. A method of killing or damaging unwanted plants comprising applying a composition as claimed in claim 25 to the foliage of the unwanted plants as a herbicide.

27. A method of killing or damaging undesired plants comprising applying a composition comprising the composition of claim 1 to the foliage of the undesired plants.

28. A method of killing targeted plants or funguses, said method comprising diluting the composition of claim 1 to below a level in which significant or irreparable damage is inflicted on desirable plants and applying the diluted composition to the targeted plants or funguses.

29. The method of claim 28, wherein the method of application maximizes the production of foam or entrapped bubbles in the applied mixture.

30. The method as claimed in claim 28, wherein the composition is applied in a manner wherein at least a monolayer of bubbles are formed over at least 50% of the leaf foliage surface area to which the composition is applied.

31. The method of claim 30, wherein application is by spray through a foam inducing nozzle.

32. The method of claim 30, wherein a half-life of the formed bubbles, based on a 50% drop in the original covered surface area, is at least 2 minutes.

33. The method of claim 32, wherein the half-life is at least 10 minutes.

34. A method of killing or damaging targeted plants, said method comprising:
   (a) preparing a composition consisting essentially of:
      (i) a monoterpene alcohol portion comprising a pine oil with an alcohol content of at least 60% by weight; and
      (ii) a fatty acid soap from the combination of either or both tall oil, or a fatty acid compound, with an alkali metal compound, wherein said agricultural composition comprises sufficient fatty acid soap and/or sufficient foam enhancing agent to allow the composition to be applied as, or to produce, a foam having at least a surface monolayer of bubbles during use; and
   (b) applying the composition to the foliage of said targeted plants as a selective foliar applied herbicide, wherein said composition is diluted to a range defined by observable thresholds with an upper limit being the concentration for significant or irreparable damage to desirable plants, and a lower limit being no significant damage to targeted plants, wherein the desirable plants are crop plants, forest plants, lawn plants, plantation plants or orchard plants.

35. The method of claim 34, wherein the upper limit is defined by 10% or more of desirable plants being killed, and the lower limit by less than 10% or more of targeted plants being killed.

36. A method of treating an insect pest comprising:
   (a) preparing an agricultural composition comprising:
      (i) a monoterpene alcohol portion comprising a pine oil with an alcohol content of at least 60% by weight; and
      (ii) a fatty acid soap from the combination of either or both tall oil, or a fatty acid compound, with an alkali metal compound, wherein said agricultural composition comprises sufficient fatty acid soap and/or sufficient foam enhancing agent to allow the composition to be applied as, or to produce, a foam having at least a surface monolayer of bubbles during use, and
   (b) diluting the agricultural composition with water to a concentration below a threshold in which there is significant herbicidal action; and
   (c) applying the agricultural composition in the vicinity of an insect pest.

* * * * *